(12) United States Patent
Mori et al.

(10) Patent No.: US 9,956,427 B2
(45) Date of Patent: May 1, 2018

(54) MOVING-BODY TRACKING DEVICE FOR RADIATION THERAPY, IRRADIATION REGION DETERMINING DEVICE FOR RADIATION THERAPY, AND RADIATION THERAPY DEVICE

(71) Applicant: SHIMADZU CORPORATION, Kyoto (JP)

(72) Inventors: Shinichiro Mori, Chiba (JP); Yoshiyuki Yamagishi, Kyoto (JP); Yui Torigoe, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days. days.

(21) Appl. No.: 15/646,164

(22) Filed: Jul. 11, 2017

(65) Prior Publication Data

US 2017/0312544 A1  Nov. 2, 2017

Related U.S. Application Data

(62) Division of application No. 15/118,614, filed as application No. PCT/JP2015/052967 on Feb. 3, 2015, now Pat. No. 9,724,540.

(30) Foreign Application Priority Data

Feb. 24, 2014 (JP) .................................. 2014-032888

(51) Int. Cl.
*A61N 5/10* (2006.01)
*A61B 6/03* (2006.01)

(52) U.S. Cl.
CPC ............ *A61N 5/1037* (2013.01); *A61B 6/032* (2013.01); *A61N 5/1039* (2013.01); *A61N 5/1077* (2013.01)

(58) Field of Classification Search
CPC .... A61B 6/032; A61N 5/1037; A61N 5/1039; A61N 5/1049; A61N 5/1077; A61N 2005/1061
See application file for complete search history.

(56) References Cited

U.S. PATENT DOCUMENTS 6,307,914 B1  10/2001  Kunieda et al.
6,385,288 B1   5/2002  Kanematsu
(Continued)

FOREIGN PATENT DOCUMENTS

JP       3053389      6/2000
JP    2002210029      7/2002
(Continued)

OTHER PUBLICATIONS

PCT/JP2015/052967, International Search Report and Written Opinion dated May 12, 2015, 8 pages—English, 9 pages—Japanese.

*Primary Examiner* — Edward Park
(74) *Attorney, Agent, or Firm* — Andrew F. Young, Esq.; Lackenbach Siegel, LLP

(57) ABSTRACT

A radiation therapy apparatus includes a radiation irradiation unit 35, an X-ray imaging unit 36, a CT imaging device 37, a treatment planning device 38, and a controller 10. The controller 10 includes a CT image deformation amount calculation unit 11, a shape calculation unit 12, an irradiation region determining unit 13, an X-ray image deformation amount calculation unit 14, a position calculation unit 15, a template matching unit 16, a comparison unit 17, a correction unit 18, and an image processing unit 19, and by comparing the positions of a treatment target locus in respective breathing phases and the positions of the treatment target locus in corresponding ones of the respective breathing phases identified by the template matching unit (Continued)

16, identifies the error values between the positions and the positions identified by the template matching unit 16 for each of parameters.

2 Claims, 8 Drawing Sheets

(56) References Cited

U.S. PATENT DOCUMENTS

| | | |
|---|---|---|
| 2006/0165211 A1* | 7/2006 | Goto .................. A61B 6/032 378/4 |
| 2008/0081991 A1 | 4/2008 | West et al. |
| 2011/0044429 A1* | 2/2011 | Takahashi ............ A61N 5/103 378/65 |
| 2011/0317896 A1 | 12/2011 | Huber et al. |
| 2015/0055848 A1 | 2/2015 | Huber et al. |

FOREIGN PATENT DOCUMENTS

| | | |
|---|---|---|
| JP | 2008-80131 | 4/2008 |
| JP | 2013529509 | 7/2013 |
| WO | WO 2011/163411 | 12/2011 |

* cited by examiner

MOVING-BODY TRACKING DEVICE FOR RADIATION THERAPY, IRRADIATION REGION DETERMINING DEVICE FOR RADIATION THERAPY, AND RADIATION THERAPY DEVICE

CROSS REFERENCE TO RELATED APPLICATIONS

This application relates to and is a divisional of U.S. Ser. No. 15/118,614 filed Aug. 12, 2016, which in turn is a national phase of and claims § 371 priority from SN PCT/JP2015/052967 filed Feb. 3, 2015, the entire contents of which are incorporated herein by reference, which in turn claims priority to JP Ser. No. 2014-032888 filed Feb. 24, 2014.

FIGURE FOR PUBLICATION

FIG. 6

BACKGROUND OF THE INVENTION

Field of the Invention

Technical Field

The present invention relates to a moving body tracking device for radiation therapy and an irradiation region determining device for radiation therapy, and a radiation therapy apparatus thereof used for a radiation therapy that treats a patient by irradiating the patient with a treatment beam. Specifically, the moving body tracking device refers to a device that performs target tracking that tracks a target as a moving body moving along with patient's breathing or the like, and thereby tracks the position of the moving body.

Background Art

In radiation therapy that irradiates an affected area such as a tumor with radiation such as an X-ray or an electron beam, it is necessary to accurately irradiate the affected area with the radiation. However, the affected area may move along with patient's breathing. For example, a tumor near a lung largely moves on the basis of breathing. For this reason, there is proposed a radiation therapy apparatus configured to arrange a metallic marker near a tumor, detect the position of the marker using an X-ray fluoroscope, and control the irradiation of treatment radiation (see Patent Literature 1).

Further, in recent years, there has also been proposed markerless tracking that can omit inserting a marker into the body of a patient by, instead of using a marker, performing the image recognition of the position of a specific locus such as a tumor.

Still further, there is also proposed a method that prepares radiation treatment planning using four-dimensional CT image data that contains a group of three-dimensional images taken at different times (see Patent Literature 2).

CITATION LIST

Patent Literature

Patent Literature 1: Japanese Patent No. 3053389
Patent Literature 2: JP-2008-80131 A

ASPECTS AND SUMMARY OF THE INVENTION

Technical Problem

In any of the case of the marker tracking that uses a metallic marker arranged inside the body of a patient as a target and the case of the markerless tracking that utilizes a specific locus of a patient as a target, in order to perform such target tracking, it is necessary to recognize the position of the target using image processing. In addition, the accuracy of the target tracking depends on setting parameters used when performing the target tracking. The appropriate values of the parameters depending on an individual patient are also different and therefore appropriately setting the parameters is extremely difficult and requires a lot of experience.

The present invention is made in order to solve the above problem, and a first object thereof is to provide a moving body tracking device for radiation therapy and a radiation therapy apparatus that allow the parameters used when performing the target tracking to be easily set.

Also, in order to identify the position and shape of a treatment target locus, information on the position and shape of the treatment specific locus in a preliminarily obtained reference breathing phase should be corrected in accordance with the body motion of a patient due to patient's breathing. Doing this work manually not only requires a lot of working hours but also causes an error.

The present invention is made in order to solve the above problem, and a second object thereof is to provide an irradiation region determining device for radiation therapy and a radiation therapy apparatus that allow the position and shape of a treatment target locus, which are taken along with the body motion of a patient, to be easily identified.

Solution to Problem

According to a first aspect of the present invention, a moving body tracking device used for radiation therapy that treats a patient by irradiating the patient with a treatment beam comprises: an X-ray image information acquisition unit that acquires a position of a treatment target locus in a referential breathing phase and three-dimensional X-ray image data consisting of a group of two-dimensional X-ray image data of a region, including the treatment target locus, in multiple successive breathing phases from a storage device; an X-ray image deformation amount calculation unit that calculates a deformation amount of a two-dimensional X-ray image including the treatment target locus between different breathing phases by performing image registration on the three-dimensional X-ray image data acquired from the storage device, and thereby; a position calculation unit that calculates positions of the treatment target locus in the respective breathing phases on the basis of the position of the treatment target locus in the referential breathing phase acquired from the storage device and the deformation amount of the two-dimensional X-ray image including the treatment target locus between the different breathing phases calculated by the X-ray image deformation amount calculation unit; a template matching unit that acquires X-ray images of a region including the treatment target locus in the multiple successive breathing phases, prepares templates used when performing tracking by setting parameters for template matching, and performs operations, identification of the positions of the treatment target locus in the respective breathing phases, multiple times changing the parameters;

and a comparison unit that compares the positions of the treatment target locus in the respective breathing phases calculated by the position calculation unit and the positions of the treatment target locus in the respective breathing phases identified by the template matching unit and identifies error values due to every each parameter or combination thereof.

According to a second aspect of the present invention, the parameters include the number of the templates acquired during one breathing cycle and/or a threshold value used for the template matching.

According to a third aspect of the present invention, a moving body tracking device further comprises an image processing unit that displays graphically relationships between the number of the templates acquired during a breathing cycle and/or the threshold value used for the template matching and the error values when changing the number of the templates acquired during a breathing cycle and/or the threshold value used for the template matching.

A fourth aspect of the present invention is such that the image processing unit graphically displays a two-dimensional color map that represents the error values in different colors with the number of the templates acquired during a breathing cycle and the threshold value used for the template matching as a vertical axis and a horizontal axis, respectively on the display unit.

A fifth aspect of the present invention further comprises; a treatment planning storage unit that stores a shape of the treatment target locus in the referential breathing phase and four-dimensional CT image data consisting of a group of three-dimensional CT image data of the region including the treatment target locus in the multiple successive breathing phases; a CT image deformation amount calculation unit that performs image registration on the four-dimensional CT image data acquired from the treatment planning storage unit, and thereby calculates a deformation amount of a three-dimensional CT image including the treatment target locus between different breathing phases; a shape calculation unit that calculates shapes of the treatment target locus in the respective breathing phases on the basis of the shape of the treatment target locus in the reference breathing phase stored in the treatment planning storage unit, and the deformation amount of the three-dimensional CT image including the treatment target locus between the different breathing phases calculated by the CT image deformation amount calculation unit; an irradiation region determining unit that determines a treatment beam irradiation region on the basis of the shapes of the treatment target locus in the respective breathing phases calculated by the shape calculation unit; and a treatment beam irradiation control unit that emits the treatment beam with use of the treatment beam irradiation region determined by the irradiation region determining unit and positions of the treatment target locus obtained by, in the template matching unit, performing the template matching with use of the parameters that have been corrected on the basis of the error values identified by the comparison unit.

A sixth aspect of the present invention is a radiation therapy apparatus including the moving body tracking device for radiation therapy according to any of the first to fifth aspects of the present invention.

A seventh aspect of the present invention is an irradiation region determining device for a treatment beam used for a radiation therapy apparatus that treats a patient by irradiating the patient with the treatment beam, and comprises: a treatment planning acquisition unit adapted to, from a storage device, acquire a shape of a treatment target locus in a reference breathing phase and four-dimensional CT image data consisting of a group of pieces of three-dimensional CT image data of a region including the treatment target locus in multiple successive breathing phases; a CT image deformation amount calculation unit that performs the image registration on the four-dimensional CT image data acquired from the storage device, and thereby calculates a deformation amount of a three-dimensional CT image including the treatment target locus between different breathing phases; a shape calculation unit that calculates shapes of the treatment target locus in the respective breathing phases on the basis of the shape of the treatment target locus in the referential breathing phase acquired from the storage device, and the deformation amount of the three-dimensional CT image including the treatment target locus between the different breathing phases calculated by the CT image deformation amount calculation unit; and an irradiation region determining unit that determines a treatment beam irradiation region on the basis of the shapes of the treatment target locus in the respective breathing phases calculated by the shape calculation unit.

An eighth aspect of the present invention is a radiation therapy apparatus including the irradiation region determining device for radiation therapy according to the seventh aspect of the present invention.

Advantageous Effects of Invention

According to the first, second, third, and sixth aspects of the present invention, the parameters used when performing the target tracking can be easily set with high accuracy.

According to the fourth aspect of the present invention, the relationships between the number of the templates acquired during the one breathing cycle and the threshold value used for the template matching, and the error values between the positions of the treatment target locus in the respective breathing phases calculated by the position calculation unit and the positions of the treatment target locus in corresponding ones of the respective breathing phases identified by the template matching unit can be easily recognized through the graphic display.

According to the fifth, seventh, and eighth aspects of the present invention, the positions and shapes of the treatment target locus, which are taken along with the body motion of the patient, can be easily identified by using the image registration.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
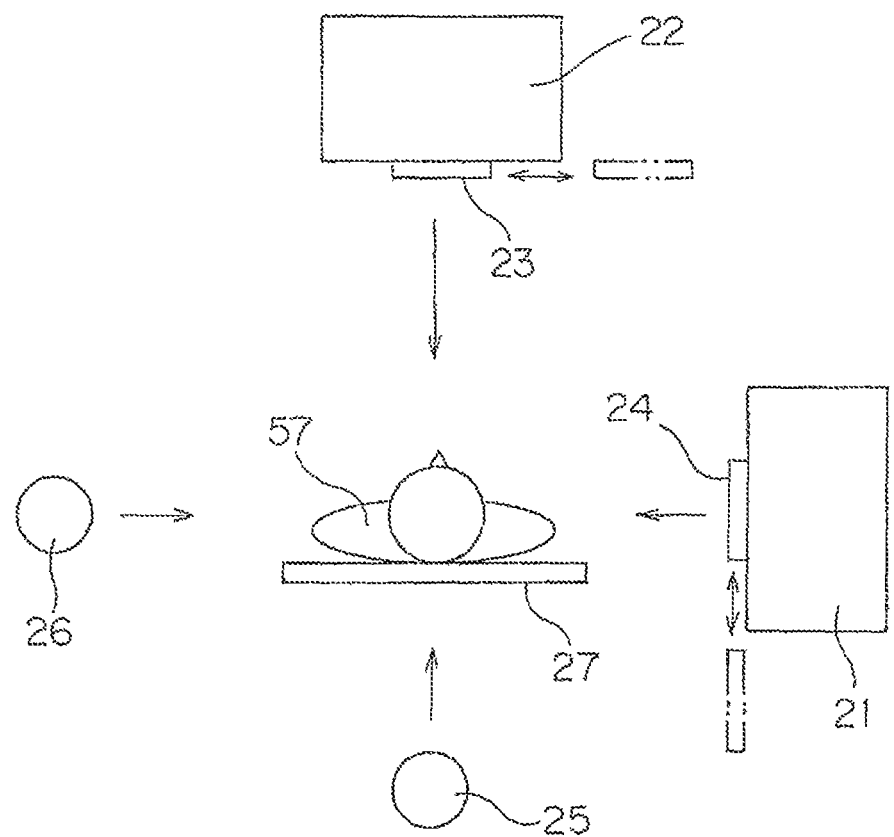
FIG. 1 is a schematic diagram of a radiation therapy apparatus according to the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 2:
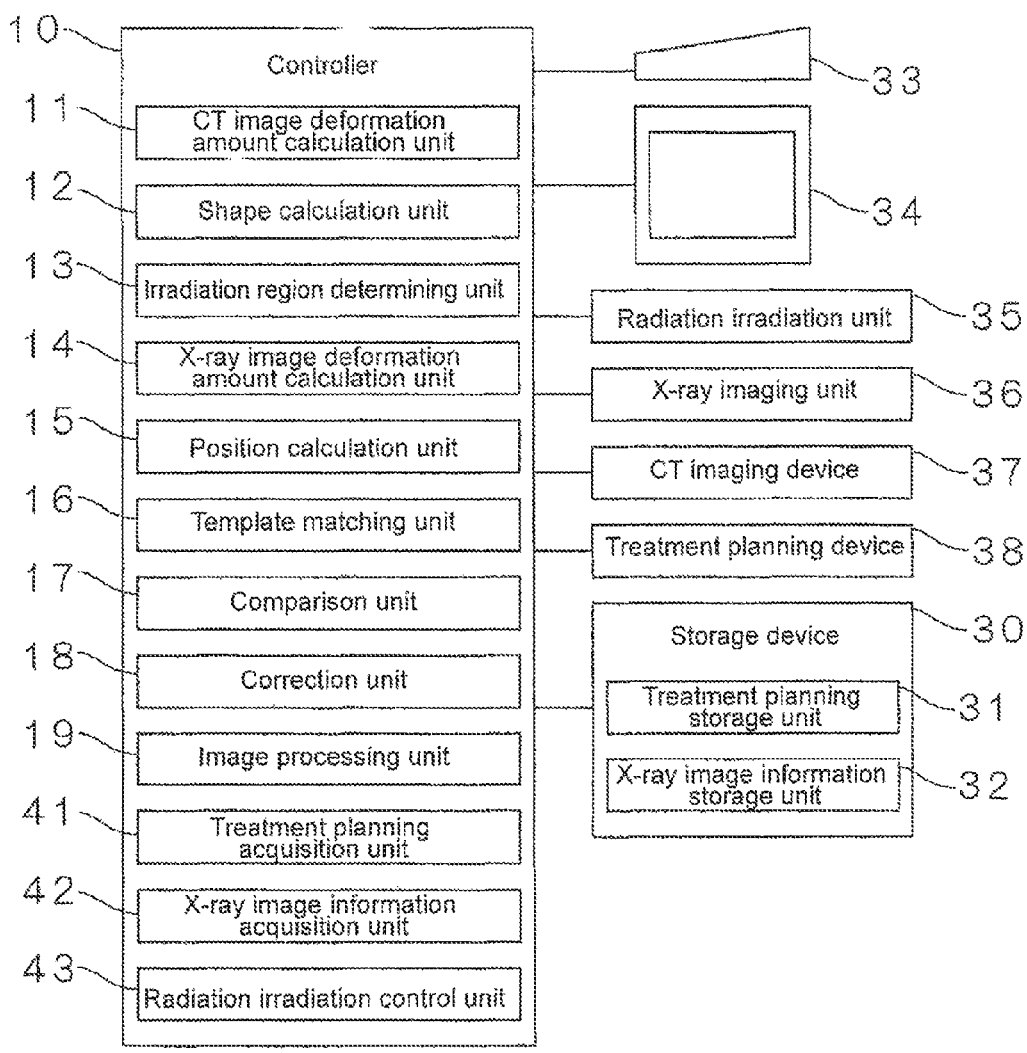
FIG. 2 is a block diagram of the radiation therapy apparatus according to the present invention.

Embodiments of the present invention will hereinafter be described on the basis of the drawings. FIG. 1 is a schematic diagram of a radiation therapy apparatus according to the present invention, and FIG. 2 is a block diagram illustrating the main control system of the radiation therapy apparatus. Further, a radiation irradiation unit 35 and an X-ray imaging unit 36 constituting the radiation therapy apparatus are independent devices and include controllers, respectively; however, FIG. 2 illustrates the functional configuration of the whole of the radiation therapy apparatus as the block diagram. Also, a configuration excluding a storage device 30, a radiation irradiation unit 35, a CT imaging device 37, and a treatment planning device 38 from the radiation therapy apparatus in FIG. 2 is the configuration of the moving body tracking device for radiation therapy or irradiation region determining device for radiation therapy according to the present invention.

The radiation therapy apparatus includes a treatment table 27 for placing a patient 57. The treatment table 27 is capable of moving and rotating in six-axis directions. Also, the radiation therapy apparatus includes the radiation irradiation unit 35 having a horizontal irradiation port 21 and a vertical irradiation port 22, each of which emits radiation such as an X-ray or an electron beam. Further, the radiation therapy apparatus includes the X-ray imaging unit 36 having: a pair of X-ray tubes 25 and 26; and a pair of X-ray detectors 23 and 24 for measuring X-rays that have been emitted from the X-ray tubes 25 and 26 and passed through the patient 57. In addition, as each of the X-ray detectors 23 and 24, for example, an image intensifier (I. I.) or a flat panel detector (FPD) is used.

Still further, the radiation therapy apparatus includes: the CT imaging device 37 that takes CT images of the patient 57; the treatment planning device 38 that prepares treatment planning for the patient 57; the storage device 30 that is connected to an in-hospital system and the like through a network to store various pieces of data of the patient 57; an input unit 33 including a keyboard and a mouse; and a display unit 34 including a liquid crystal display panel and the like. In addition, the whole of the radiation therapy apparatus is controlled by a controller 10.

The horizontal irradiation port 21 and the vertical irradiation port 22 are fixed in an examination laboratory. Also, the X-ray detector 24 is movable between an imaging position in front of the horizontal irradiation port 21 facing to the X-ray tube 26 through the patient 57 and a withdrawn position spaced from the horizontal irradiation port 21, and the X-ray detector 23 is movable between an imaging position in front of the vertical irradiation port 22 facing to the X-ray tube 25 through the patient 57 and a withdrawn position spaced from the vertical irradiation port 22.

The CT imaging device 37 takes three-dimensional CT images of the patient 57 and provides the CT images including the affected area of the patient 57 prior to performing radiation therapy. The CT images taken by the CT imaging device 37 are sent to the treatment planning device 38, and the treatment planning is prepared on the basis of the pieces of patient data read from the storage device 30 and the three-dimensional CT images taken by the CT imaging device 37 in the treatment planning device 38. In addition, the three-dimensional CT images of the patient 57 are taken during at least one breathing cycle of the patient 57. Further, four-dimensional CT image data consisting of a group of three-dimensional CT image data of a region including a treatment target locus in multiple successive breathing phases is stored in a treatment planning storage unit 31 in the storage device 30 together with the shape of the treatment target locus in a reference breathing phase as a part of the treatment planning.

Also, when preparing the treatment planning, the acquisition of X-ray images is performed on the patient 57 by the X-ray imaging unit 36 (although it is possible to employ X-ray imaging or X-ray fluoroscopy, the following description is given on the assumption of employing the X-ray fluoroscopy). The X-ray fluoroscopy is performed on the patient 57 during at least the one breathing cycle of the patient 57. In addition, three-dimensional X-ray image data consisting of a group of two-dimensional image data of the region including the treatment target locus in the multiple successive breathing phases is stored in an X-ray image information storage unit 32 in the storage device 30 together with the position of the treatment target locus in the benchmark reference breathing phase.

The above-described controller 10 includes: a CT image deformation amount calculation unit 11 that calculates the deformation amount of a three-dimensional CT image including the treatment target locus between different breathing phases; a shape calculation unit 12 that calculates the shapes of the treatment target locus in the respective breathing phases; an irradiation region determining unit 13 that determines a treatment beam irradiation region; an X-ray image deformation amount calculation unit 14 that calculates the deformation amount of a two-dimensional X-ray image including the treatment target locus between different breathing phases; a position calculation unit 15 that calculates the positions of the treatment target locus in the respective breathing phases; a template matching unit 16 that identifies the positions of the treatment target locus in the respective breathing phases by template matching; a comparison unit 17 that compares the positions of the treatment target locus in the respective breathing phases calculated by the position calculation unit 15 and the positions of the treatment target locus in corresponding ones of the respective breathing phases identified by the template matching unit 16 to identify the error values therebetween; a correction unit 18 that corrects parameters on the basis of the error values; and image processing unit 19 that graphically displays a two-dimensional color map, which represents the error values in different colors, on the display unit 34.

Also, the controller 10 includes: a treatment planning acquisition unit 41 that acquires the four-dimensional CT image data and the shape of the treatment target locus in the benchmark reference breathing phase from the treatment planning storage unit 31; an X-ray image information acquisition unit 42 adapted to acquire the three-dimensional X-ray image data and the position of the treatment target locus in the reference breathing phase from the X-ray image information storage unit 32; and a radiation irradiation control unit 43 that controls the radiation irradiation unit 35 to emit the radiation as a treatment beam.

Figure 3:
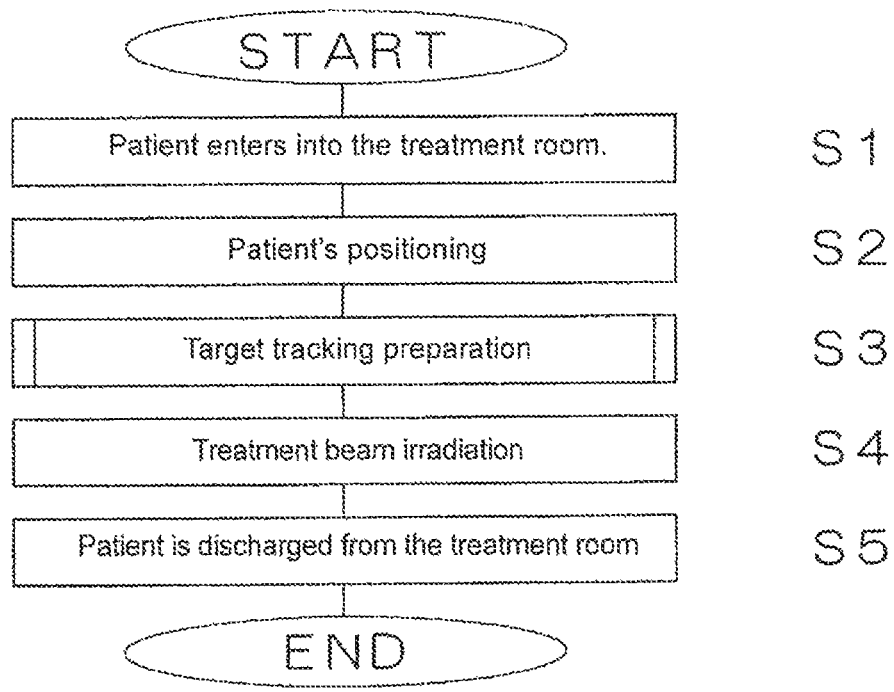
FIG. 3 is a flowchart illustrating the basis steps of radiation therapy.

Next, steps of conducting a radiation therapy in accordance with which the radiation therapy is performed using the above-described radiation therapy apparatus will be described. First, the basic steps of the radiation therapy will be described. FIG. 3 is a flowchart illustrating the basic steps of the radiation therapy.

When performing the radiation therapy, after the patient 57 has entered the treatment room (Step S1), the patient 57 is positioned (Step S2). After the patient 57 has been positioned in a position appropriate for the therapy, target tracking is prepared (Step S3). After that, the radiation irradiation unit 35 receives an instruction from the radiation irradiation control unit 43 to emit the radiation as the treatment beam (Step S4). Then, when a necessary treatment is finished, the patient 57 is discharged from the treatment room (Step S5).

Figure 4:
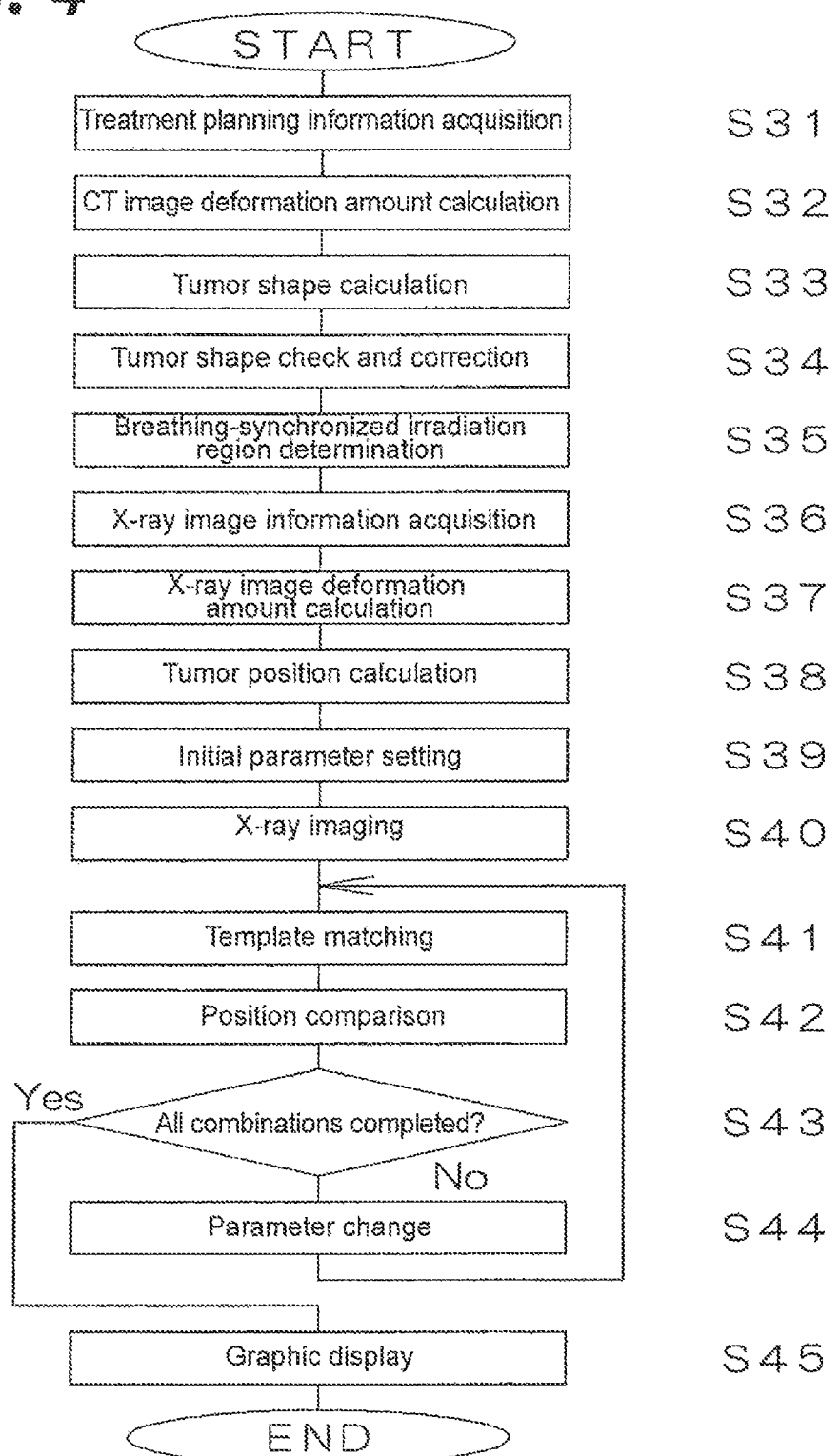
FIG. 4 is a flowchart illustrating a target tracking preparation step.

Next, the above-described target tracking preparation step (Step S3) will be described. FIG. 4 is a flowchart illustrating the target tracking preparation step. Further, the following description is regarding the case in which the treatment target locus is a tumor of the patient 57.

When preparing the target tracking, the treatment beam irradiation region is first set. At this time, the treatment planning acquisition unit 41 in the controller 10 acquires treatment planning information from the treatment planning storage unit 31 in the storage device 30 (Step S31). The treatment planning information is recorded in RT-DICOM (Digital Imaging and Communication in Medicine). Also, from the treatment planning information, the shape of the tumor to be treated and the four-dimensional CT image data are acquired. Here, the four-dimensional CT image data is data consisting of the group of the pieces of three-dimensional CT image data of the region including the tumor in the multiple successive breathing phases.

In addition, at this time, the data of the shape of an organ containing the tumor can be acquired together, and the shape of the tumor and the like can be superposed on CT data in the benchmark reference breathing phase, and the superposition is displayed, which can be checked by an operator.

Subsequently, the CT image deformation amount calculation unit 11 performs image registration on the four-dimensional CT image data acquired from the treatment planning storage unit 31, and thereby calculates the deformation amount of a three-dimensional CT image including the tumor between different breathing phases (Step S32). More specifically, nonlinear registration is performed on the CT image data in the respective breathing phases to thereby calculate the deformation amount (3D-Vector) of CT image data between the respective breathing phases.

Then, the shape calculation unit 12 calculates the shapes of the tumor in the respective breathing phases on the basis of the shape of the tumor in the referential breathing phase stored in the treatment planning storage unit 31 in the storage device 30 and the deformation amount of the three dimensional CT image including the tumor between the different breathing phases calculated by the CT image deformation calculation unit 11 (Step S33).

After that, the calculated shapes of the tumor are superposed on the three-dimensional CT images in the respective breathing phases and displayed, and the operator checks a shape in each of the respective breathing phases to correct it as necessary (Step S34).

Subsequently, the irradiation region determining unit 13 prepares a region that is based on the shapes of the treatment target locus in the respective breathing phases and added with a margin based on respiratory displacement to determine the breathing-synchronized irradiation region of the treatment beam by the radiation irradiation unit 35 (Step S35). Irradiation with the treatment beam using the below-described template matching is performed within the irradiation region.

Figure 5:
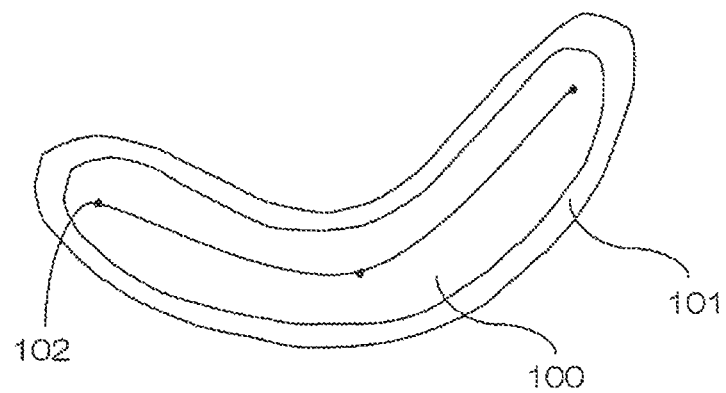
FIG. 5 is an explanatory diagram illustrating an irradiation region synchronized with breathing.

FIG. 5 is an explanatory diagram illustrating the breathing-synchronized irradiation region.

The shapes of the tumor in the respective breathing phases have been already calculated. A region obtained by adding a margin region 101 based on the respiratory displacement to a gating window 100 that is a region to be irradiated with the treatment beam around the positions 102 of the tumor in the respective breathing phases is determined as the breathing-synchronized irradiation region.

Then, parameters for preparing templates used for the target tracking are optimized to prepare the templates. At this time, the X-ray image information acquisition unit 42 in the controller 10 acquires X-ray image information from the X-ray image information storage unit 32 in the storage device 30 (Step S36). In addition, the position of the tumor to be treated and the three-dimensional X-ray image data are acquired from the X-ray image information. Further, the three-dimensional X-ray image data is data consisting of the group of the two-dimensional X-ray image data of the region including the tumor in the multiple successive breathing phases.

Subsequently, the X-ray image deformation amount calculation unit 14 calculate the deformation amount of a two-dimensional X-ray image including the tumor between different breathing phases by performing image registration on the three-dimensional X-ray image data acquired from the X-ray image information storage unit 32 (Step S37). More specifically, the deformation amount (2D-Vector) of X-ray image data between the respective breathing phases is calculated by performing nonlinear registration on the X-ray image data in the respective breathing phases.

Next, the position calculation unit 15 calculates the positions of the tumor in the respective breathing phases on the basis of the position of the tumor in the referential breathing phase stored in the X-ray image information storage unit 32 and the deformation amount of the two-dimensional X-ray image including the tumor between the different breathing phases is calculated by the X-ray image deformation amount calculation unit 14 (Step S38).

Then, the template matching unit 16 sets the initial values of the parameters for the template matching (Step S39). As such parameters in the present embodiment, the number of templates acquired during the one breathing cycle and the threshold value used for the template matching are adopted.

Specifically, a parameter as to how many templates are prepared during the one breathing cycle of the patient 57 is employed as the first parameter. As such templates, when performing marker tracking, images including a metallic marker are used, and when performing markerless tracking, images including a specific locus (tumor) used in place of a marker are used. The target tracking is performed by performing the template matching using the prepared multiple templates.

Also, as the second parameter, the threshold value used for the template matching is employed. The threshold value refers to reliability used for the template matching, in other words, when performing the template matching, how the degree of matching between a template and the target as the marker or the specific locus is required to recognize that the template is the target.

Then, on the basis of the set parameters, the template matching unit 16 acquires X-ray images of the region including the tumor as the treatment target locus (the images are not particularly limited but in the present embodiment, X-ray fluoroscopic images) to thereby prepare the templates used when performing the tracking, as well as acquiring X-ray images of the region including the tumor in the multiple successive breathing phases (the images are not particularly limited, but in the present embodiment, X-ray fluoroscopic images) (Step S40), and performs the template matching on the successively acquired X-ray images using the prepared templates to thereby identify the positions of the treatment target locus in the respective breathing phases (Step S41).

Figure 6:
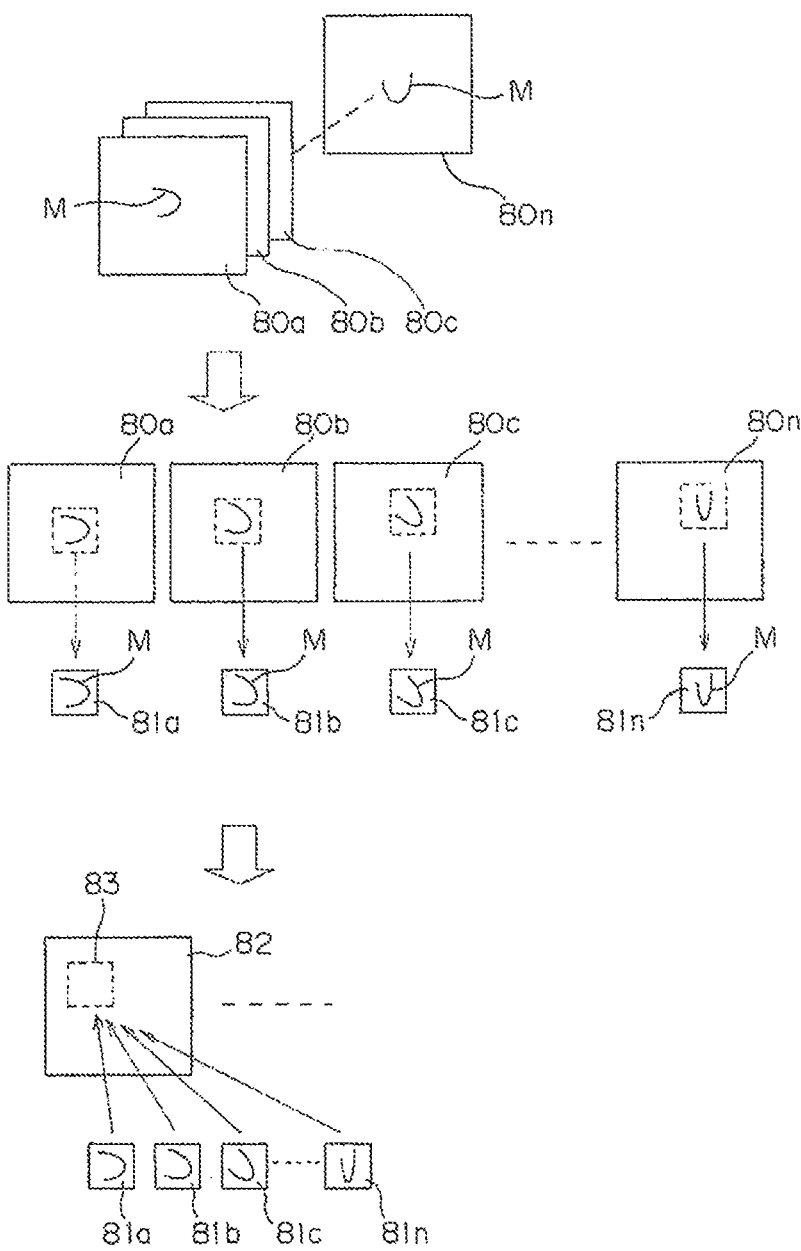
FIG. 6 is an explanatory diagram illustrating a template matching action.

FIG. 6 is an explanatory diagram illustrating a template matching operation described above. In FIG. 6, the images used for the template matching are denoted by a symbol M. Further, when performing the markerless tracking using the specific locus such as the tumor, images of the specific locus such as the tumor are used as the images M. On the other hand, when performing the marker tracking using the marker, images of the metallic marker are used as the images M.

When preparing the templates respectively including the images M, by successively fluoroscoping the patient 57, images 80a, 80b, 80c, . . . , 80n respectively including the images M are acquired. At this time, the images 80a, 80b, 80c, . . . , 80n respectively including the images M are acquired by fluoroscoping the patient 57 during at least the one breathing cycle of the patient 57, for example, at a frame rate of approximately 30 fps (flames per second). Then, from the images 80a, 80b, 80c, . . . , 80n respectively including the images M, image M portions are extracted to obtain template images 81a, 81b, 81c, . . . , 81n. At this time, the images over which an image M moves are acquired with breathing of the patient 57. For this reason, as illustrated in FIG. 6, the acquired images M are sequentially deformed.

At this time, the number of the template images 81a, 81b, 81c, . . . , 81n prepared during the one breathing cycle is one of the above-described parameters.

Subsequently, at the frame rate of approximately 30 fps, a region including an image M is fluoroscoped. Then, the template matching is performed on the region 83 including the image M in an image 82 acquired at the regular intervals using the multiple template images 81a, 81b, 81c, . . . , 81n. Specifically, all of the multiple template images 81a, 81b, 81c, . . . , 81n are sequentially matched with the region 83 including the image M in the image 82 acquired at the regular intervals.

When any of the multiple template images 81a, 81b, 81c, . . . , 81n exceeds the threshold value preset for the matching, it is determined that the matching is successful. Further, when some template images among the multiple template images 81a, 81b, 81c, . . . , 81n exceed the threshold value, a template image having the highest matching degree thereamong is recognized as a matched template image.

This time, the threshold value used for the template matching is one of the above-described parameters.

Referring to FIG. 4 again, the comparison unit 17 compares the positions of the tumor in the respective breathing phases calculated by the position calculation unit 15 and the positions of the treatment target locus in corresponding ones of the respective breathing phases identified by the template matching unit 16 to calculate error values (Step S42). Until all of preset parameter combination conditions are completed (Step S43), after the correction unit 18 has changed the above-described two parameters (Step S4), the steps of Steps S41 to S43 are repeated. Specifically, as the parameters, the number of templates acquired during the one breathing cycle and the threshold value used for the template matching are changed to prepare templates and the operation of performing the template matching on the X-ray images previously successively acquired by the fluoroscope using the templates is repeated multiple times with the use of the templates while changing the parameters so that error values for each of the parameters can be calculated.

On the other hand, when the error values between the positions of the tumor in the respective breathing phases calculated by the position calculation unit 15 and the positions of the treatment target locus in the respective breathing phases identified by the template matching unit 16 have been calculated for all combinations of the parameters (Step S43), the image processing unit 19 graphically displays the two-dimensional color map representing the error values in different colors on the display unit 34 (Step S45).

Figure 7:
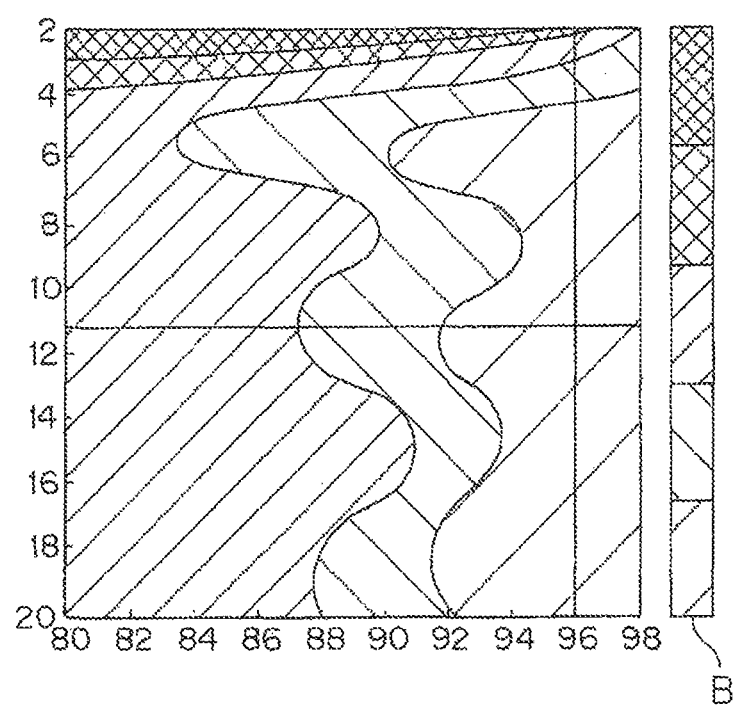
FIG. 7 is a schematic diagram of a two-dimensional color map graphically displayed on a display unit 34.
Figure 8:
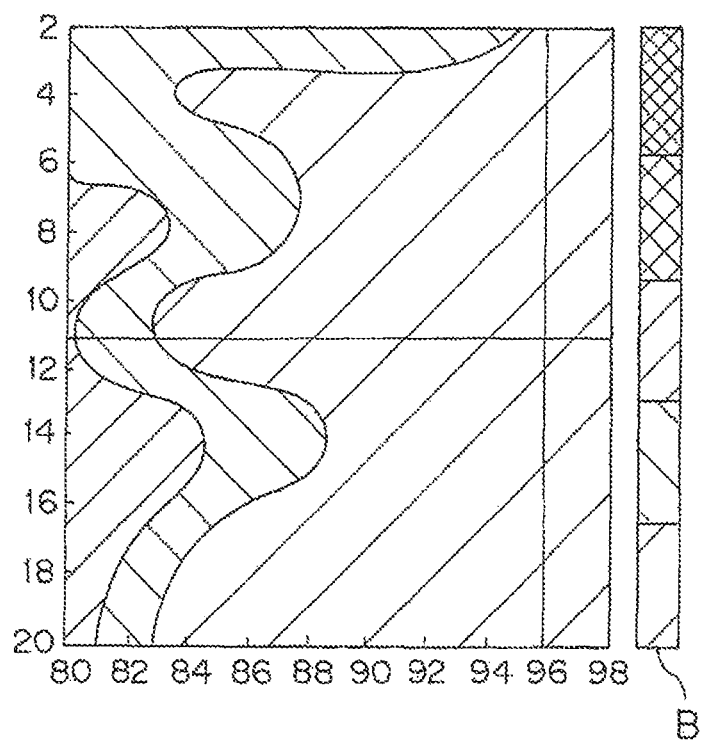
FIG. 8 is a schematic diagram of the two-dimensional color map graphically displayed on the display unit 34.

FIG. 7 and FIG. 8 are schematic diagrams of the two-dimensional color map graphically displayed on the display unit 34. In addition, FIG. 7 and FIG. 8 illustrate the two-dimensional color maps along mutually orthogonal directions (directions respectively corresponding to a detecting direction by the X-ray detector 23 and a detecting direction by the X-ray detector 24 in FIG. 1).

In each of the diagrams, the different colors are schematically represented by hatching patterns. Also, in each of the diagrams, the vertical axis represents the number of templates prepared during the one breathing cycle of the patient 57, and the horizontal axis represents the threshold value used for the template matching. Further, in a color (hatching pattern) band B in each of the diagrams, a region where the error is larger is given upward. Still further, in each of the diagrams, the intersection area between mutually orthogonal straight lines displayed in the two-dimensional color map indicates a region where the error is the smallest. These two straight lines are displayed on the basis of arithmetic results by the comparison unit 17. Further, an operator may designate the two straight lines.

By graphically displaying such a two-dimensional color map on the display unit 34, the relationships between the number of the templates acquired during the one breathing cycle and the threshold value used for the template matching as the parameters, and the error values between the positions of the treatment target locus in the respective breathing phases calculated by the position calculation unit 15 and the positions of the treatment target locus in corresponding ones of the respective breathing phases identified by the template matching unit 16 can be easily recognized.

The above-described steps complete the target tracking preparation step (Step S3) including the treatment beam irradiation region setting, the parameter optimization, and the template preparation. The above-described treatment beam irradiation (Step S4) is performed using the treatment beam irradiation region and the templates based on the optimized parameters obtained in the target tracking preparation step.

Further, without limitation to the above-described embodiment, modification is also possible as follows. Specifically, until the error values between the positions of the tumor in the respective breathing phases calculated by the position calculation unit 15 and the positions of the treatment target locus in corresponding ones of the respective breathing phases identified by the template matching unit 16 fall within an allowable range, after the correction unit 18 has changed the above-described two parameters, S41 to S43 are repeated. When the error values between the positions of the tumor in the respective breathing phases calculated by the position calculation unit 15 and the positions of the treatment target locus in corresponding ones of the respective breathing phases identified by the template matching unit 16 fall within the allowable range, the parameters are automatically determined.

REFERENCE SIGNS LIST

10 Controller
11 CT image deformation amount calculation unit
12 Shape calculation unit
13 Irradiation region determining unit
14 X-ray image deformation amount calculation unit
15 Position calculation unit
16 Template matching unit
17 Comparison unit
18 Correction unit
19 Image processing unit
21 Horizontal irradiation port
22 Vertical irradiation port
23 X-ray detector
24 X-ray detector
25 X-ray tube
26 X-ray tube
27 Treatment table
31 Treatment planning storage unit
32 X-ray image information storage unit
34 Display unit
35 Radiation irradiation unit
36 X-ray imaging unit
37 CT imaging device
38 Treatment planning device
41 Treatment planning acquisition unit
42 X-ray image information acquisition unit
43 Radiation irradiation control unit
57 Patient
80a to 80n Images acquired by fluoroscopy
81a to 81n Template images
82 Image acquired by fluoroscopy
83 Region including image M
100 Gating window
101 Margin region based on respiratory displacement
102 Positions of tumor in respective breathing phases Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An irradiation region determining device for radiation therapy, wherein the irradiation region determining device for a treatment beam is used for a radiation therapy apparatus that treats a patient by irradiating the patient with the treatment beam, comprising:
    a treatment planning acquisition circuit that acquires a shape of a treatment target locus in a reference breathing phase and four-dimensional CT image data consisting of a group of pieces of three-dimensional CT image data of a region including the treatment target locus in multiple successive breathing phases from a storage device;
    a CT image deformation amount calculation circuit that performs image registration on the four-dimensional CT image data acquired from the storage device, and thereby calculate a deformation amount of a three-dimensional CT image including the treatment target locus between different breathing phases;
    a shape calculation circuit that calculates shapes of the treatment target locus in the respective breathing phases on a basis of the shape of the treatment target locus in the reference breathing phase, the shape being acquired from the storage device, and the deformation amount of the three dimensional CT image including the treatment target locus between the different breathing phases, the deformation amount being calculated by the CT image deformation amount calculation circuit; and
    an irradiation region determining circuit that determines a treatment beam irradiation region on a basis of the shapes of the treatment target locus in the respective breathing phases, the shapes being calculated by the shape calculation circuit.

2. The irradiation region determining device, according to claim 1, further comprising:
    a radiation therapy apparatus that generates said treatment beam.

* * * * *